Figure 1:
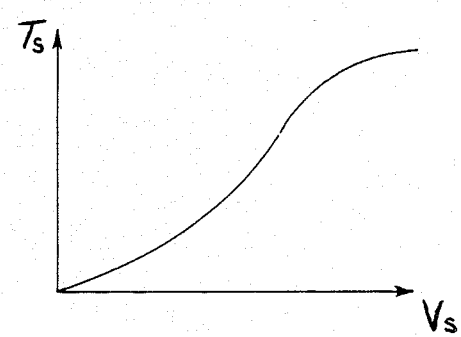

United States Patent [19]

Chidzey et al.

[11] Patent Number: 4,570,054
[45] Date of Patent: Feb. 11, 1986

[54] OPEN LOOP CONTROL FOR SPECTROPHOTOMETER ATOMIZER FURNACE

[75] Inventors: John A. Chidzey, Cheltenham; John T. Huberts, Mount Waverley, both of Australia

[73] Assignee: Varian Associates, Inc., Palto Alto, Calif.

[21] Appl. No.: 708,368

[22] Filed: Mar. 5, 1985

Related U.S. Application Data

[63] Continuation of Ser. No. 344,267, Jan. 28, 1982, abandoned.

[30] Foreign Application Priority Data

Jan. 29, 1981 [AU] Australia .............................. PE7403

[51] Int. Cl.[4] .............................................. H05B 1/02
[52] U.S. Cl. .................................... 219/490; 219/492; 219/497; 219/501; 340/589; 323/319; 323/322
[58] Field of Search ............... 219/492, 490, 491, 502, 219/507–510, 497, 501, 413; 236/15 BB; 374/134; 323/299, 300, 319, 322; 340/588, 589

[56] References Cited

U.S. PATENT DOCUMENTS

| | | | |
|---|---|---|---|
| 4,046,991 | 9/1977 | Setton et al. | 219/497 |
| 4,159,876 | 7/1979 | Egan et al. | 356/312 |
| 4,300,037 | 11/1981 | Padden | 219/492 |
| 4,334,147 | 6/1982 | Payne | 219/492 |
| 4,340,807 | 7/1982 | Raskin et al. | 219/501 |
| 4,367,399 | 1/1983 | Anthony et al. | 219/492 |
| 4,404,461 | 9/1983 | Sitek et al. | 323/319 |
| 4,433,232 | 2/1984 | Tachikawa et al. | 219/502 |

Primary Examiner—M. H. Paschall
Attorney, Agent, or Firm—Stanley Z. Cole; Edward H. Berkowitz

[57] ABSTRACT

Heating apparatus particularly for flameless atomization in spectrophotometers includes a variable electrical power source and a resistive heating element. A desired final temperature and the rate of change of the element temperature (ramp rate) is input to a control circuit. A storage means is provided for storing data relating the heating element temperature to the energy input (voltage) to the heating element required to maintain the heating element at a constant temperature. Processing means calculates from the various data the voltage required to be supplied to the element by the power source to change the temperature thereof at the selected ramp rate until it reaches the final temperature. In spectrophotometers the apparatus accurately controls the carbon rod temperature through drying, ashing and atomizing stages.

11 Claims, 2 Drawing Figures

OPEN LOOP CONTROL FOR SPECTROPHOTOMETER ATOMIZER FURNACE

This application is a continuation of application Ser. No. 344,267, filed Jan. 28, 1982, now abandoned.

This invention relates to heating apparatus having some control of the temperature changes in resistive heating elements. It is to be understood that "heating" covers both increasing and decreasing the temperature of the elements.

The invention has been particularly designed for use in flameless atomization of materials, and is especially applicable in chemical analysis equipment such as spectrophotometers, but may have other uses such as in metallurgical or ceramic processes where fine temperature control is required. It will be convenient to hereinafter describe the invention in relation to atomic absorption spectrophotometers.

In atomic absorption spectrophotometers employing flameless atomization, the atomizer is often formed by a carbon element, and the sample to be analysed is deposited on or within that element usually in the form of a solution. Atomization of the sample in the light path of the instrument results in the production of an absorption signal and the peak height or area of the signal is usually taken as a measure of the concentration of the element of interest in the sample solution. Under ideal conditions, the peak height or area of the signal is linearly related to concentration.

During analysis of a sample, the temperature of the atomizer is increased through a range having at its lowest level a temperature below that necessary to dry the sample solvent and at its upper level a temperature sufficient to atomize the sample. In fact several samples are atomized in turn during the course of a normal analysis programme, and the accuracy of the analysis is dependant upon the uniformity of the conditions existing at the atomizer during each atomization step. It is found however, that the temperature conditions of the atomizer vary between the atomization steps, and that variation has an adverse effect on the accuracy of the analysis.

A method and apparatus is described in Australian Pat. No. 497,605 in which the voltage supplied to the heating element of an atomizer is controlled by a feedback circuit which includes means for generating an electrical analogue of the heating response characteristics of the element. This includes compensation for the delay in response of the element to a change in supplied voltage. This prior apparatus is accurate only at a certain temperature and rate of temperature change (ramp rate) and would require adjustment to give precise results at other temperatures or ramp rates. This inaccuracy results in part from the approximation that the incremental voltage required to heat the element at a steady rate is linearly related to that heat rate.

It is an object of the present invention to provide apparatus for controlling temperature changes of a heating element in a precise and reproducable manner. A preferred object of the present invention is to provide apparatus for accurately controlling the rate of increase of the temperature of a heating element of the atomizer of chemical analysis apparatus.

In broad terms, the present invention relies on the use of electronic circuitry whereby a resistive heating element is energized in a controlled manner such as to achieve a temperature/time profile of a particular form, and which form can be reproduced with substantial accuracy in subsequent energizations of the element. The temperature/time profile of the element is to be understood as equivalent to a physical representation of the temperature variation of the element as plotted against the time. It is to be further understood that the concept of the invention is applicable in conditions of either rising or falling temperature, although it has been designed for rising temperature conditions in flameless atomization spectroscopic apparatus, i.e. upwards through the dry, ash and atomizing temperature range.

According to the present invention there is provided heating apparatus including an electrical power source, a resistive heating element arranged to generate heat by being supplied with electrical energy from the power source, said power source being variable to enable control of the energy supplied to the element thereby controlling its temperature and a control circuit operable to determine the energy required to change the temperature of the element at a particular rate and to generate an output signal to which the power source is responsive so as to control the energy supplied by the power source to the heating element.

Preferably the control circuit includes storage means for storing data relating the heating element temperature to the energy input to the heating element required to maintain the heating element at a constant temperature.

Also the control circuit preferably includes processing means coupled to the storage means and operable to determine the energy input required to be supplied to the heating element by the power source to change the temperature thereof at a selected rate until it reaches a predetermined final temperature.

In one embodiment the processing means is operable to calculate an average steady energy required to achieve a predetermined temperature change of the heating element, the calculation being made from the selected rate of temperature change, the final temperature, the initial temperature of the heating element, and the data stored in the storage means.

When the heating apparatus is used in a chemical analysis apparatus, such as a spectrophotometer, the heating element comprises a carbon rod, and the control circuit is operable to control the rate of temperature change of the carbon rod through the drying, ashing and atomizing stages.

Figure 2:
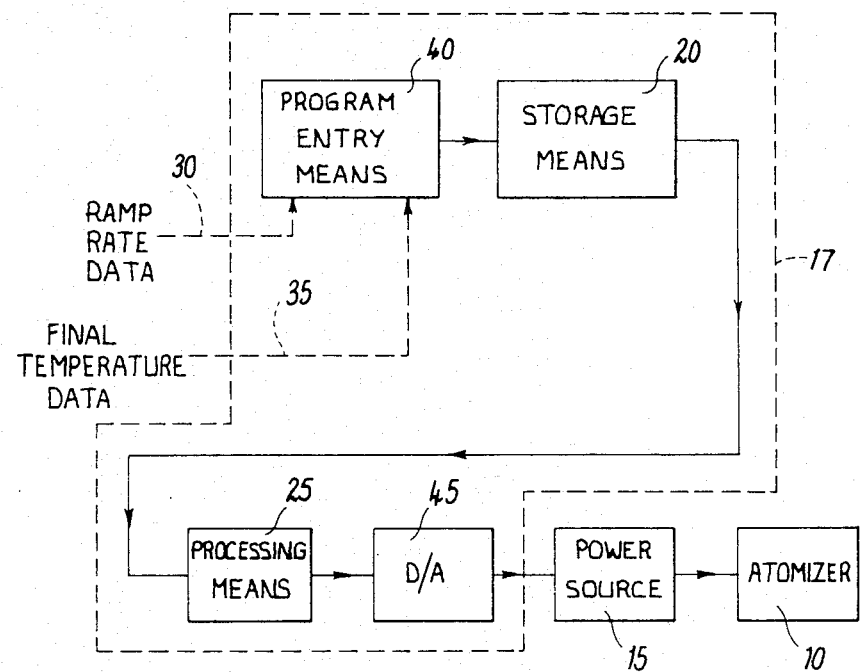

An example embodiment of heating apparatus according to the present invention is shown in the accompanying drawings, in which:

FIG. 1 is a plot of the stored steady voltage versus steady temperature characteristics of a resistive element, and FIG. 2 is a block diagram of apparatus according to the present invention.

Referring to the drawings, the heating apparatus includes an electrical power source 15 and a resistive heating element 10 arranged to generate heat by being supplied with electrical energy from the power source 15. The power source 15 is variable to enable control of the energy supplied to the element 10 thereby controlling its temperature. The element 10 in the case of flameless atomization spectrophotometers may be a carbon rod which is arranged to be energized so as to be heated through various stages corresponding to drying, ashing and atomizing of a liquid sample introduced into the apparatus. The power source 15 is variable and may be arranged to supply a constant voltage and be variable by changing the periods during which the source 15 is supplying energy to the element 10. However, preferably the power source 15 is arranged to supply a continuous voltage of selectively variable level.

The heating apparatus also includes a control circuit 17 operable to determine the energy required to change the temperature of the element 10 at a particular rate and to generate an output signal to which the power source 15 is responsive so as to control the energy supplied by the power source 15 to the element 10. The term "energy" is used in this context not according to its technical definition but in a general sense so as to include other parameters such as voltage, current and power.

The control circuit 17 includes storage means 20 for storing the temperature response characteristics of the resistive element 10. The storage means 20 may be arranged to store the characteristics in digital form. For example, the storage means may comprise a programmable read-only memory (ROM). Preferably the stored temperature response characteristics comprise data relating the heated element temperature to the energy input to the heating element 10 required to maintain the element at a constant temperature. For example, the data stored may correspond to a plot of the required steady current or power input required versus steady temperature. However, preferably the data is representative of a plot of the required steady voltage to maintain the element at a steady temperature as shown in FIG. 1. The provision of the storage means 20 enables non-linear relationships between voltage and temperature to be stored and used in the apparatus. The data may be read into the ROM comprising the storage means 20 from manufacturer's data or during calibration of the apparatus before a heating process is begun, such as when a new element is installed in the apparatus.

The control circuit 17 further includes input means 40 for providing input signals representative of a selected rate of change of temperature required and also a predetermined final temperature required to be reached by the element 10. The temperatures required in the case of flameless atomization spectrophotometers may correspond to dry, ash and atomize temperatures for the element 10. The input means 40 is variable so that an operator of the apparatus can preselect and feed in on line 30 a desired rate of change of temperature, (ramp rate) and on line 35 the final temperature required. The input means 40 is shown as a programme entry means from which the final temperature and temperature change rate data can be read into the storage means 30.

The control circuit 17 further includes processing means 25 coupled to the storage means 20 and operable to determine the energy input required to be supplied to the element 10 by the power source 15 to change the temperature of the element 10 at the selected rate until it reaches the predetermined final temperature. The processing means 25 may be continuously operable so as to calculate the energy input required at predetermined intervals by reading the required rate of temperature change and final temperature required from the input means 40 and consulting the element temperature response characteristics data stored in the storage means 20 at each interval so as to update the output signal to the power source 15 to maintain or appropriately vary the output thereof to the heating element 10.

In an alternative and preferred embodiment, the processing means 25 is operable to calculate only once the energy input required to change the element temperature at a predetermined rate until it reaches the predetermined final temperature. In this embodiment, the processing means 25 is operative to calculate from (a) the selected rate of temperature change, (b) the predetermined final temperature, (c) the initial temperature of the element 10, and (d) data stored in the storage means 20, an average steady energy required to achieve the temperature change at the predetermined rate. The processing means 25 may also be operable to generate a signal switching the power source 15 to a constant output required to maintain the element 10 at the final temperature when the element 10 reaches that temperature. This signal may be generated either after a predetermined time or when the final temperature is sensed by a temperature measuring means (not shown).

In the preferred embodiment the processing means 25 is operative to generate a level signal representative of the required voltage output of the power source and to which the power source is responsive. In this preferred embodiment where the processing means 25 is operative to calculate the required voltage output of the power source, the processing means 25 may be operative to calculate $V_t$ according to the following formula:

$$V_t = ((V_s)^2 + S \cdot R \cdot R_e)^{\frac{1}{2}} \tag{1}$$

where $V_t$ is the voltage required to be supplied by the power source 15 to the element 10, $V_s$ is the voltage required to maintain the element 10 at the steady temperature from which the change of temperature of the element starts, S is the specific heat of the element 10 in joules/°K., R is the selected rate of change of the element temperature in °K./second, and $R_e$ is the resistance of the element 10 in ohms. This relationship is derived in the following manner.

Assuming that the specific heat of the element 10 remains relatively constant over the required temperature range, the energy required to change the temperature of the element 10 is defined by:

$$E = S \cdot \Delta T \tag{2}$$

where E=energy in joules, S=specific heat in joules/°K., and $\Delta T$=change in temperature °K.

If it is desired to change the temperature of the element 10 at a certain rate R, then the power required to effect this change is given by:

$$R = \frac{\Delta T}{\Delta t} \tag{3}$$

where R=ramp rate in °K./seconds, $\Delta t$=change in time in seconds.

$$P_r = \frac{E}{\Delta t}$$

$P_r$=ramp power in watts. From equations (2) and (3):

$$P_r = S \cdot \frac{\Delta T}{\Delta t}$$

∴ $P_r = S \cdot R$. Thus the power required to ramp the element temperature is directly proportional to the ramp rate.

The Total Power ($P_t$) required to ramp from temperature $T_s$ at rate R is then;

$$P_t = P_s + P_r$$

where $P_s$ is power required to maintain steady state temperature and $$P_s = \frac{(V_s)^2}{R_e}$$

where $R_e$ = electrical resistance $$\therefore P_t = \frac{(V_s)^2}{R_e} + S \cdot R.$$

If voltage feedback control is used, this power must be converted to voltage $V_t$. Now $$P_t = \frac{(V_t)^2}{R_e}$$

$\therefore V_t = (P_t \cdot R_e)^{\frac{1}{2}}$, i.e., $V_t = ((V_s)^2 + S \cdot R \cdot R_e)^{\frac{1}{2}}$. This expression may be evaluated by the processing means 25 to generate the output signal to the power source 15. The signal may be passed through a digital to analogue converter 45 if required.

In the case of the embodiment where the processing means 25 continuously updates the output signal to the power source 15, $V_t$ is continuously calculated at predetermined intervals substantially shorter than $\Delta t$ to maintain the temperature of the element 10 changing at the selected rate. This may be achieved by reading the programmed element temperature at a pre-set rate, and calculating $V_t$ from the stored voltage ($V_s$) versus temperature (T) characteristics by reading the $V_s$ for the particular read element temperature and calculating $V_t$ from equation (1) to apply the signal representing the update $V_t$ to the power source 15. As soon as the final temperature ($T_{s+\Delta t}$) is reached $V_t$ is switched to the voltage ($V_{s+\Delta t}$) required to maintain the resistive element 10 at that temperature according to the stored characteristics.

In the embodiment where the processing means works by a single approximation calculation, $V_s$ in equation (1) corresponding to the starting temperature of the element 10. The processing means 25 then calculates an average $V_t$ required to change the temperature at the selected rate R. The processing means 25 is then operative, after the calculated time interval $\Delta t$ or when the final temperature is reached, to switch the power source 15 over to the steady voltage $V_{s+\Delta t}$ required to maintain the resistive element 10 at the final predetermined temperature according to the stored $V_s$ versus $T_s$ characteristics.

Having now described our invention, what we claim as new and desire to secure by Letters Patent is:

1. Heating apparatus for spectrophotometric analysis apparatus comprising:
    an electrical power source,
    a resistive heating element arranged to generate heat by being supplied as electrical energy from the power source, said power source being variable to enable control of the energy supply to the element, thereby controlling its temperature, and a control circuit operable to determine the total energy required to monotonically change the temperature of the element from an initial temperature to a selectable final temperature at a particular selectable rate, said total energy being dependent on the energy input to the heating element required to maintain the heating element at a constant temperature and also being dependent on said particular rate of element temperature change, said control circuit including storage means for storing data relating the heating element temperature within a temperature range to the energy input to the heating element at a constant temperature, both said initial temperature and said selectable final temperature falling within said temperature range, and said control circuit being operable to determine said total energy in part from said data in said storage means, and in part from the selected said particular rate of element temperature change, said control circuit being operable to generate an output signal representative of said total energy and to which the power source is responsive so as to control the energy supply by the power source to the heating element.

2. Heating apparatus according to claim 1 wherein the control circuit includes input means for providing input signals representative of a selected rate of temperature change and also a predetermined final temperature required to be reached by the heating element.

3. Heating apparatus according to claim 2 wherein said control circuit includes processing means coupled to the storage means and operable to determine the energy input required to be supplied to the heating element by the power source to change the temperature thereof at the selected rate until it reaches the final temperature.

4. Heating apparatus according to claim 3 wherein the processing means is operable to calculate an average steady energy required to achieve a predetermined temperature change of the heating element, the calculation being made from the selected rate of temperature change, the final temperature, the initial temperature of the heating element, and the data stored in the storage means.

5. Heating apparatus according to claim 3 or 4 wherein the processing means is operable to generate a signal switching the power source to a constant energy output required to maintain the heating element at the final temperature when the element reaches said final temperature.

6. Heating apparatus according to claim 5 wherein the energy is a voltage level and the processing means is operable to generate a level signal representative of the required voltage level, the power source being responsive to the level signal.

7. Heating apparatus according to claim 6 wherein the processing means is operable to calculate $V_t$, being the voltage required to be supplied by the power source, according to the following formula:

$$V_t = (C_s)^2 + S \cdot R \cdot R_e)^{\frac{1}{2}}$$

where $V_s$ is the voltage required to maintain the heating element at the temperature from which the change of temperature starts, S is the specific heat of the heating element in joules/°k., R is the selected rate of temperature change in °k./second, and $R_e$ is the resistance of the heating element in ohms.

8. A chemical analysis apparatus including heating apparatus according to claim 1 and for the purpose of heating a chemical sample through drying, ashing, and atomizing stages, said heating element comprising a carbon rod, said control circuit being operable to control the rate of temperature change of the carbon rod through the drying, ashing and atomizing stages.

9. A method for controlled heating of a sample for spectrophotometric studies, to raise the temperature of said sample as a desired monotonic function of time from an initial temperature to a final temperature in an open loop regime, comprising the steps of determining a first component of electrical power for thermal dissipation to the sample at its surrounds, said first component comprising the quantity of electrical power required to maintain said initial temperature of said sample and its surrounds, and applying said first component to said sample at its surrounds, assertaining a second component of electrical power, additive to said first component, said second component comprising the quantity of electrical power required to raise the temperature of said sample at its surrounds to said final temperature at a desired rate $dT/dt$ and applying said second component to said sample at its surrounds.

10. The method claim 9 further comprising:

continuing to apply said second component until a condition is reached which corresponds to said desired final temperature, redetermining a magnitude of electrical power for dissipation to said sample and its surrounds, said magnitude comprising the quantity of power required to maintain said final temperature of said sample at its surrounds, and supplying said redetermined magnitude of electrical power.

11. The method of claim 10 comprising:

counting the time interval during which said second component of power is applied, thereby monitoring said condition.

* * * * *